United States Patent
Coates et al.

(10) Patent No.: US 7,300,994 B2
(45) Date of Patent: Nov. 27, 2007

(54) ISOTACTIC POLYPROPYLENE CONTAINING POLYMERS

(75) Inventors: Geoffrey W Coates, Ithaca, NY (US); Andrew F. Mason, Los Gatos, CA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/261,920

(22) Filed: Oct. 31, 2005

(65) Prior Publication Data

US 2006/0111528 A1    May 25, 2006

Related U.S. Application Data

(60) Provisional application No. 60/629,347, filed on Nov. 22, 2004.

(51) Int. Cl.
*C08F 210/06* (2006.01)
*C08F 110/06* (2006.01)
*C08F 4/64* (2006.01)

(52) U.S. Cl. ............. 526/351; 526/348; 526/161; 526/165

(58) Field of Classification Search ............ 526/368, 526/351, 161, 165
See application file for complete search history.

(56) References Cited

U.S. PATENT DOCUMENTS

| 4,408,019 A | 10/1983 | Blunt ............ 525/323 |
| 4,491,652 A | 1/1985 | Matthews et al. .......... 525/247 |
| 6,838,540 B2 * | 1/2005 | Mitani et al. ............... 526/348 |
| 2004/0077815 A1 | 4/2004 | Abe ............ 526/351 |

FOREIGN PATENT DOCUMENTS

| WO | WO94/21700 | * | 9/1994 |
| WO | WO 2004/05877 A1 | * | 7/2004 |

OTHER PUBLICATIONS

Busico, V., et al., "The First Molecularly Characterized Isotactic Polypropylene-block-polyethylene Obtained via "Quasi-Living" Insertion Polymerization", Macromolecules 2003, 36, 3806-3808.
Busico, V., et al., "Block Copolymers of Highly Isotactic Polypropylene via Controlled Ziegler-Natta Polymerization", Macromolecules 2004, 37, 8201-8203—and supporting information.
Mason, A. F., et al., "New Phenoxyketimine Titanium Complexes: Combining Isotacticity and Living Behavior in Propylene Polymerization", J. Am. Chem. Soc. 2004, 126, 16326-16327—and supporting information.
Seymour, R.B., et al., "Advances in polyolefins: the world's most widely used polymers", George A. Lock article, "Thermoplastic Elastomers Based on Block Copolymers of Ethylene and Propylene", Plenum Press, New York, ISBN: 030642682X, 1987, pp. 59-74.

* cited by examiner

*Primary Examiner*—Caixia Lu
(74) *Attorney, Agent, or Firm*—Bacon & Thomas, PLLC

(57) ABSTRACT

Isotactic polypropylene homopolymers or segments of low polydispersity are prepared using phenoxyketimine catalysts containing N-pentafluorophenyl groups.

6 Claims, No Drawings

ISOTACTIC POLYPROPYLENE CONTAINING POLYMERS

CROSS REFERENCE TO RELATED APPLICATIONS

This application claims the benefit of U.S. Provisional Application No. 60/629,347, filed Nov. 22, 2004, the whole of which is incorporated herein by reference.

TECHNICAL FIELD

This invention is directed to isotactic polypropylene-containing polymers of defined polydispersity.

BACKGROUND OF THE INVENTION

Isospecific propylene polymerization has been carried out. See, e.g., Blunt (U.S. Pat. No. 4,408,019); Abe (U.S. 2004/0077815); Busico, V., et al., Macromolecules 36, 3806-3808 (2003); and Busico, V., et al., Macromolecules 37, 8201-8203 (2004). However, such polymerizations have been limited as to what polydispersities are obtained. The Busico publications are the only ones of the documents cited above that obtain polydispersities less than 1.8 and these do not obtain polydispersities less than 1.2 and obtain polydispersities of 1.2 and 1.3 only at low number average molecular weight and short reaction time (1.2 for $M_n$=6,500 g/mol and 1.3 for $M_n$=22,000 g/mol). The inability to obtain living isospecific propylene polymerization over a wide range of $M_n$ is the result of failure in the prior art to use and disclose catalysts that provide this result. While a catalyst genus is disclosed in WO 2004/058777, which embraces catalysts that have been found to provide this result, no specific catalyst is disclosed in WO 2004/058777 that provides this result and there is no indication in WO 2004/058777 that this result can be obtained. So far as method is concerned, Matthews et al. (U.S. Pat. No. 4,491,652) makes block copolymers where not all chains are living and their lifetimes are short; this is because Matthews is not privy to catalysts that are both living and isospecific.

SUMMARY OF THE INVENTION

It has been discovered herein that isotactic polypropylene-containing polymers can be prepared based on living chains, i.e., with negligible chain transfer, with lower polydispersities in each case than have been obtained heretofore, and that catalysts suitable for obtaining this result are provided within the generic disclosure but not the specific disclosure of WO 2004/058777.

One embodiment of the invention herein, denoted the first embodiment, is directed to polypropylene homopolymer having a number average molecular weight ranging from 1,000 to 1,000,000, an isotacticity defined by a [mmmm] pentad content greater than 0.20 and a polydispersity index (PDI) less than 1.2.

Another embodiment of the invention herein, denoted the second embodiment, is directed to polypropylene random or tapered copolymer where comonomer is selected from the group consisting of ethylene and $C_4$-$C_{20}$ alpha olefin, having a number average molecular weight ranging from 1,000 to 1,000,000 and a PDI less than 1.5 for the entire polymer and an isotacticity for $C_3$-$C_{20}$ alpha olefin segments defined by a [mmmm] pentad content greater than 0.20.

Another embodiment of the invention herein, denoted the third embodiment, is directed to block copolymer having one to five polypropylene blocks with an isotacticity defined by a [mmmm] pentad content greater than 0.20 and a PDI of less than 1.8 and having number average molecular weight ranging from 1,000 to 1,000,000, and one to five atactic polypropylene blocks having number average molecular weight ranging from 1,000 to 1,000,000.

Another embodiment of the invention herein, denoted the fourth embodiment, is directed to block copolymer having one or more polypropylene blocks with an isotacticity defined by a [mmmm] pentad content greater than 0.20 and having a PDI of less than 1.8 and having a number average molecular weight ranging from 1,000 to 1,000,000 and one or more non-homopolyethylene blocks and non-polypropylene blocks having a number average molecular weight ranging from 1,000 to 1,000,000. As used herein, the term "non-homopolyethylene" means any polymer that does not solely consist of ethylene; the term "non-polypropylene" means any polymer that does not solely consist of propylene.

Another embodiment of the invention herein, denoted the fifth embodiment, is directed to block copolymer having one polypropylene block having isotacticity defined by [mmmm] pentad content greater than 0.2 and having a number average molecular weight of at least 1,000, and one polyethylene block having a number average molecular weight of at least 1,000 where the block copolymer has PDI less than 1.2 and number average molecular weight ranging from 2,000 to 6,500 g/mol, or has a PDI less than 1.3 and number average molecular weight ranging from greater than 6,500 to 22,000 g/mol or has PDI of less than 4 and number average molecular weight ranging from greater than 22,000 to 1,000,000.

Another embodiment of the invention herein, denoted the sixth embodiment, is directed to a process for preparing a block copolymer with one or more isotactic polypropylene blocks and one or more different blocks from other monomer or comonomer mixtures where the monomer or comonomer is selected from the group consisting of ethylene, $C_3$-$C_{20}$ alpha-olefin, $C_4$-$C_{20}$ cyclic olefin (e.g. cyclopentene or norbornene), and alpha-omega ($C_3$-$C_{10}$) dienes, e.g., 1,5-hexadiene, and mixtures thereof, comprising the step(s) of polymerizing propylene in the presence of a catalyst that is both living and isospecific, in the presence of polymer or copolymer formed from polymerization of said monomer or comonomer mixtures or followed by polymerization of said monomer or comonomer mixtures in the presence of propylene polymerization product. The term "catalyst that is both living and isospecific" is used herein to refer to a catalyst which rapidly initiates, has negligible chain transfer and produces repeat units predominantly of the same relative stereochemistry.

Another embodiment of the invention herein, denoted the seventh embodiment, is directed to compound having the structure

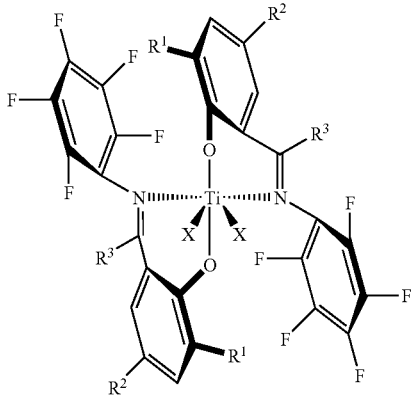

(I)

where $R^3$ is selected from the group consisting of $C_6$-$C_{20}$ aryl, $C_1$-$C_{20}$ halocarbon and $C_1$-$C_{20}$ alkyl; $R^1$ is selected from the group consisting of $C_6$-$C_{20}$ aryl, $C_1$-$C_{20}$ alkyl, $C_1$-$C_{20}$ halocarbon, halogen (e.g., chlorine, bromine or iodine), $C_1$-$C_{20}$ alkoxide, $C_1$-$C_{20}$ amide and $C_1$-$C_{20}$ acyl and $R^2$ is selected from the group consisting of H, $C_6$-$C_{20}$ aryl, $C_1$-$C_{20}$ alkyl, $C_1$-$C_{20}$ halocarbon, halogen (e.g., chlorine, bromine or iodine), $C_1$-$C_{20}$ alkoxide, $C_1$-$C_{20}$ amide, and $C_1$-$C_{20}$ acyl, with the proviso that $R^1$ and $R^2$ are not both tert-butyl and in one case $R^2$ being H and $R^1$ being tert-butyl is excepted; and X is selected from the group consisting of halogen (e.g., Cl, Br, I), H, $C_1$-$C_{20}$ alkyl, $C_6$-$C_{20}$ aryl and $OR^4$ and $NR^4_2$ where $R^4$ is $C_1$-$C_{20}$ alkyl.

The compounds are useful as living and isospecific catalysts in the first, second, third and fourth embodiments herein.

Number average molecular weight ($M_n$), weight average molecular weight ($M_w$) and polydispersities ($M_w/M_n$) are determined by high-temperature gel-permeation chromatography (GPC) in 1,2,4-trichlorobenzene at 140° C. versus polyethylene standards.

Lower PDI is important because it connotes longer chain lifetimes and allows control over the $M_n$ of the polymer.

DETAILED DESCRIPTION

In the first, second, third, fourth and fifth embodiments where the isotacticity is defined by [mmmm] pentad content greater than 0.20, the [mmmm] pentad content is preferably greater than 0.30, very preferably greater than 0.40, e.g., greater than 0.50 or greater than 0.60.

We turn now to the first embodiment of the invention herein. The polypropylenes of the first embodiment can be prepared, e.g., in a pressure reactor maintained at 1 to 1,000 psi propylene pressure during polymerization, e.g., in the presence of catalyst as defined in the seventh embodiment herein, e.g., at a turnover frequency (mol propylene/mol Ti.h) ranging from 5 to 2000 in an amount of catalyst per mole of propylene ranging, for example, from 1 to $1\times10^{-6}$ mmol per mole. The catalyst of the seventh embodiment is preferably used in the presence of activator, i.e., compound that reacts with the titanium complex constituting the catalyst to generate an active catalytic species in situ. The activator is used in an amount in large excess with respect to the amount of catalyst used. The activator is preferably methylaluminoxane (MAO) used in an amount, e.g., such that [Al]:[Ti] in terms of molar ratio ranges from 100 to 200:1, e.g., 125 to 175:1. Times of reaction range, for example, from 1 to 48 hours at reaction temperatures ranging from minus 80 to plus 100° C. A general reaction for preparation of polypropylene homopolymer of the first embodiment according to the present invention is:

Preparations of propylene homopolymers of the first embodiment are illustrated in Working Example IV. Catalysts used in Working Example IV are indicated below.

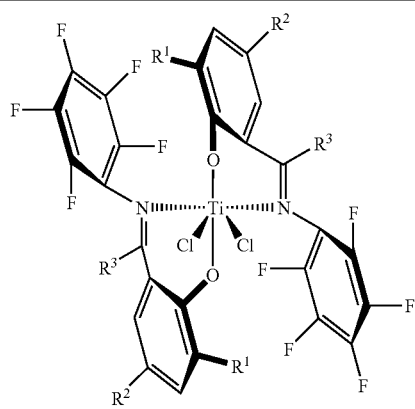

| Complex | $R^1$ | $R^2$ | $R^3$ |
|---|---|---|---|
| 1 | $^t$Bu | $^t$Bu | Ph |
| 2 | $^i$Pr | $^i$Pr | Ph |
| 3 | Et | Me | Ph |
| 4 | Me | Me | Ph |
| 5 | H | Me | Ph |
| 6 | Me | Me | H |

We turn now to the second embodiment herein. The copolymer of the second embodiment can be prepared as follows: The propylene and comonomer are both introduced into a pressure reactor maintained at 1 to 1,000 psi in the presence of catalyst as defined in the seventh embodiment in an amount of catalyst per mole of monomer ranging from 1 to $1\times10^6$ mmol per mole. The catalyst is preferably used in the presence of large excess of activator, e.g., methylaluminoxane (MAO) in an amount of [Al]:[Ti] molar ratio ranging from 100 to 200:1, e.g., 125 to 175:1. The reaction is carried out, for example, for 1 to 48 hours at minus 80 to plus 100° C.

We turn now to the third embodiment herein. The polymerization is carried out initially by polymerizing propylene to form isotactic polypropylene; then the reaction conditions are changed (e.g., the temperature is raised) to produce an atactic polypropylene block. The times of reactions are the same as for the first embodiment.

We turn now to the fourth embodiment of the invention herein. The non-homopolyethylene/homopolypropylene blocks can be, for example, ethylene/propylene copolymer blocks, ethylene/cyclopentene blocks, ethylene/norbornene blocks, hexadiene blocks or propylene/hexene blocks. Where propylene is one of the constituents of the non-homopolyethylene/non-homopolypropylene block, the block copolymer is readily made by the method of the fifth embodiment herein, e.g., initially polymerizing to form isotactic polypropylene and then adding other monomer, e.g., ethylene, to continue the polymerization to form a second block with catalyst and activators being the same as for the first embodiment but with the ratio of catalyst to monomers ranging, for example, from 1 to $1 \times 10^{-6}$ mmols/mole, and the amount of activator, reaction temperature, and reaction time being the same as for the first embodiment. A general reaction for preparation of isotactic polypropylene-block-ethylene/propylene copolymer is set forth below:

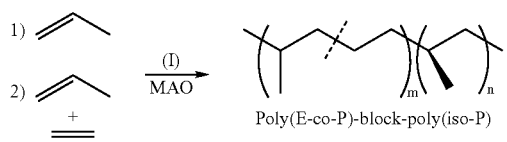

Poly(E-co-P)-block-poly(iso-P)

A general procedure for synthesis of isotactic polypropylene-block-ethylene/propylene copolymer is as follows. A six-ounce Lab-Crest pressure reaction vessel (Andrews Glass) equipped with a magnetic stir bar is charged with dry PMAO-IP (polymethylaluminoxane in toluene available from Akzo) (150 equivalents Al per Ti) and toluene (100 mL). The reactor is then equilibrated at 0° C. and the solution was saturated with propylene (30 psi). A toluene solution (5 mL) of phenoxyimine (PHI) catalyst (0.04 mmol) is injected via syringe to initiate the polymerization. A constant pressure of propylene (30 psi) is maintained for 4 hours. An aliquot of isotactic polypropylene is removed from the reactor via cannula and quenched with methanol. The reactor is placed under ethylene pressure (35 psi), and the polymerization is continued for 3.0 minutes at 0° C. The polymerization is quenched with methanol (5 mL) and the reactor is vented. The polymer is precipitated in copious methanol/HCl (1% acid, 300 mL), collected, washed with methanol, and dried to constant weight.

The fourth embodiment is illustrated by Working Example V.

We turn now to the fifth embodiment of the invention herein. Block copolymers of the fifth embodiment are readily made by initially polymerizing to form isotactic polypropylene and after all the propylene is consumed or removed, adding ethylene to continue the polymerization to form a second block, with catalyst and activators being the same as for the first embodiment but with the ratio of catalyst to monomers ranging, for example, from 1 to $1 \times 10^6$ mmols/mole. The amount of activator, reaction temperature and reaction time are the same as for the first embodiment.

We turn now to the sixth embodiment herein. This method can be used to make isotactic polypropylene-ethylene propylene diblock copolymer as described above. The isotactic polypropylene block can be made the same as the isotactic polypropylene of the first embodiment. The case where the second block is ethylene/propylene copolymer is described above.

We turn now to the seventh embodiment of the invention herein. Catalysts of the structure (I) where $R^1$ is $^i$Pr, $R^2$ is $^i$Pr and $R^3$ is phenyl (catalyst 2), where $R^1$ is Et, $R^2$ is Me and $R^3$ is phenyl (catalyst 3) and where $R^1$ is Me, $R^2$ is Me and $R^3$ is phenyl (catalyst 4) were shown to be functional to produce low polydispersity, highly isotactic polypropylene homopolymer or segment. Catalyst 4 was found to produce the best isotacticity results.

A general procedure for preparing the compounds of the seventh embodiment is as follows.

First, the general procedure for ketimine ligand synthesis involves adding phosphorous pentachloride (10.0 mmol) to a methylene chloride solution (75 mL) of N-pentafluorophenyl-benzemide (10.0 mmol). The resulting suspension is heated at reflux under nitrogen for 12 hours. After cooling, the solvent is removed in vacuo and the resulting white imidoyl chloride is dried to remove residual POCl$_3$. The crude imidoyl chloride is dissolved in 1,2-dichloroethane (10 mL) and transferred via cannula to a Schlenk tube containing aluminum chloride (12.0 mmol) and 1,2-dichloroethane (30 mL). A cannula is used to slowly add a solution of the desired phenol (10.0 mmol in 1,2-dichloroethane), resulting in a color change from light brown to deep orange-red. The reaction is heated at reflux under nitrogen overnight. After cooling, water (50 mL) is added; the organic layer is collected and washed with aqueous sodium carbonate solution followed by brine solution. The yellow organic layer is then dried over magnesium sulfate and filtered. The solvent is removed in vacuo to give the crude ligand as yellow oil. Specific working examples of making ligands B, C and D for making titanium complexes 2, 3 and 4 referred to above are set forth in Working Examples I, II and III, respectively.

Next, the general procedure for titanium dichloride complex synthesis entails adding n-Butyllithium (1.6 M solution in hexane, 1.05 mmol) by syringe to an ether solution of phenoxyimine ligand (1.00 mmol) at −78° C. After warming to room temperature and stirring for 15 minutes, this solution is transferred via cannula to an ether solution of TiCl$_4$ (1.0 M solution in toluene, 0.50 mmol) at −78° C. The dark red mixture is stirred at room temperature for 6 hours. After removing the solvent in vacuo, residues taken up in CH$_2$Cl$_2$ and filtered through Celite, giving a clear dark red solution. The solvent is removed and the crude product was recrystallized from CH$_2$Cl$_2$/pentane at −20° C., yielding the desired complex as red-brown crystals. Working Examples of making complexes 2, 3 and 4 are Working Examples I, II and III, respectively.

Complexes 1-5 display significantly different polymerization behavior than that previously reported for phenoxyimine catalyst systems. The addition of a seemingly remote $R^3$ substituent shifts polymer stereochemistry from slightly syndiotactic to isotactic. Complexes 1 and 5 form atactic polypropylene. Complexes 2-4 form isotactic polypropylene owing to their intermediate ligand-monomer interactions combined with appreciable facial selectivity.

Elements of the invention and Working Examples are found in Mason, A. F., and Coates, G. W., J. Am. Chem. Soc., 126, 16326-16327 (Nov. 26, 2004) and the Supporting Information associated therewith.

WORKING EXAMPLES

The invention described herein is illustrated by the following working examples.

Working Example I

Synthesis of Complex 2

For ligand B (2,4-Diisopropyl-6-[phenyl(pentafluorophenylimino)methyl]-phenol), N-Pentafluorophenyl-benzamide (1.92 g, 6.70 mmol) and phosphorous pentachloride (1.39 g, 6.70 mmol) were combined as described above to give the imidoyl chloride, which was reacted with aluminum chloride (1.07 g, 8.04 mmol) and 2,4-diisopropylphenol (1.19 g, 6.70 mmol) as described above to give the crude product as a yellow oil. This was recrystallized from methanol at −20° C. to give ligand B as a yellow crystalline solid (1.07 g, 36%). $^1$H NMR (CDCl$_3$, 300 MHz): 7.41-7.34 (m, 3H, PhH), 7.28 (d, 1H, J=2.1 Hz, ArH), 7.19 (m, 2H, PhH), 6.70 (d, 1H, J=2.1 Hz, ArH), 3.48, 2.70 (sept, 1H each, J=6.9 Hz, CHMe$_2$), 1.31, 1.09 (d, 6H each, J=6.9 Hz, CH(CH$_3$)$_2$). $^{13}$C NMR (CDCl$_3$, 125 MHz): 181.8 (C=N), 158.6 (ArC—OH), 138.8 (Ar$_F$C—F, m, $^1J_{CF}$=245 Hz), 138.5 (ArC or PhC), 138.0 (Ar$_F$C—F, m, $^1J_{CF}$=250 Hz), 137.8 (Ar$_F$C—F, m, $^1J_{CF}$=245 Hz), 137.4, 135.1, 130.4, 130.0, 128.5, 128.2, 127.1 (ArC or PhC), 124.0 (Ar$_F$C$_{ipso}$, m), 118.3 (ArC), 33.6, 27.0 (ArCHMe$_2$), 24.2, 22.7 (ArCH(CH$_3$)$_2$). $^{19}$F NMR (CDCl$_3$, 282 MHz): −149.5, −161.3, −163.4 (Ar$_F$F, m). Anal. calc. for C$_{25}$H$_{22}$NOF$_5$: C, 67.11; H, 4.96; N, 3.13. Anal. found: C, 67.04; H, 4.96; N, 3.09.

For complex 2 (Bis[2,4-Diisopropyl-6-[phenyl(pentafluorophenylimino)methyl]-phenolato]dichlorotitanium), ligand B (0.50 g, 1.12 mmol) was reacted with n-butyllithium solution (0.73 mL, 1.17 mmol) and TiCl$_4$ solution (0.56 mL, 0.56 mmol) as described above to give 2 as a red-brown crystalline solid (0.19 g, 34%). $^1$H NMR (C$_6$D$_6$, 300 MHz): 7.29 (m, 2H, PhH), 7.27 (d, 2H, J=2.1 Hz, ArH), 6.85-6.68 (m, 8H, PhH), 6.65 (d, 2H, J=2.1 Hz, ArH), 3.30, 2.34 (sept, 2H each, J=6.9 Hz, CHMe$_2$), 1.44, 1.21, 0.90, 0.89 (d, 6H each, J=6.9 Hz, CH(CH$_3$)$_2$). $^{13}$C NMR (CDCl$_3$, 125 MHz): 181.1 (C=N), 160.0 (ArC—OH), 142.0 (ArC or PhC), 139.9 (Ar$_F$C—F, m, $^1J_{CF}$=255 Hz), 138.8 (Ar$_F$C—F, m, $^1J_{CF}$=250 Hz), 137.6 (Ar$_F$C—F, m, $^1J_{CF}$=250 Hz), 137.0 (ArC or PhC), 136.8 (Ar$_F$C—F, m, $^1J_{CF}$=255 Hz), 136.2, 132.3, 130.4, 130.3, 128.5, 128.4, 126.4 (ArC or PhC), 126.2 (Ar$_F$C$_{ipso}$, m), 125.8, 123.9 (ArC), 33.8, 27.8 (ArCHMe$_2$), 24.3, 24.0, 23.7, 20.2 (ArCH(CH$_3$)$_2$). $^{19}$F NMR (CDCl$_3$, 282 MHz): −138.0, −143.7, −158.2, −161.8, −164.4 (Ar$_F$F, m). Anal. calc. for C$_{50}$H$_{42}$N$_2$O$_2$F$_{10}$Cl$_2$Ti: C, 59.36; H, 4.18; N, 2.77. Anal. found: C, 59.04; H, 4.26; N, 2.66.

Working Example II

Synthesis of Complex 3

For ligand C (2-Ethyl-4-methyl-6-[phenyl(pentafluorophenylimino)methyl]-phenol), N-Pentafluorophenyl-benzamide (2.00 g, 6.96 mmol) and phosphorous pentachloride (1.45 g, 6.96 mmol) were combined as described above to give the imidoyl chloride, which was reacted with aluminum chloride (1.11 g, 8.35 mmol) and 2-ethyl-4-methylphenol (0.95 g, 6.96 mmol) as described above to give the crude product as a yellow oil. This was recrystallized from methanol at −20° C. to give ligand C as a yellow powder (0.92 g, 33%). $^1$H NMR (CDCl$_3$, 300 MHz): 7.42-7.33 (m, 3H, PhH), 7.18 (m, 2H, PhH), 7.16. 6.65 (m, 1H each, ArH), 2.75 (q, 2H, J=7.5 Hz, CH$_2$Me), 2.14 (s, 3H, CH$_3$), 1.29 (t, 3H, J=7.5 Hz, CH$_2$CH$_3$). $^{13}$C NMR (CDCl$_3$, 125 MHz): 181.7 (C=N), 158.7 (ArC—OH), 138.7 (Ar$_F$C—F, m, $^1J_{CF}$=245 Hz), 138.0 (Ar$_F$C—F, m, $^1J_{CF}$=250 Hz), 137.7 (Ar$_F$C—F, m, $^1J_{CF}$=250 Hz), 135.8, 135.1, 133.1, 130.7, 130.0, 128.6, 127.3, 127.0 (ArC or PhC), 123.9 (Ar$_F$C$_{ipso}$, m), 118.4 (ArC), 23.1 (ArCH$_2$Me), 20.7 (ArCH$_3$), 14.1 (ArCH$_2$CH$_3$). $^{19}$F NMR (CDCl$_3$, 282 MHz): −149.6, −161.3, −163.4 (Ar$_F$F, m). Anal. calc. for C$_{22}$H$_{16}$NOF$_5$: C, 65.19; H, 3.98; N, 3.46. Anal. found: C, 65.17; H, 3.78; N, 3.34.

For complex 3 (Bis[2-Ethyl-4-methyl-6-[phenyl(pentafluorophenylimino)methyl]-phenolato]dichlorotitanium), ligand C (0.49 g, 1.21 mmol) was reacted with n-butyllithium solution (0.79 mL, 1.27 mmol) and TiCl$_4$ solution (0.60 mL, 0.60 mmol) as described above to give 3 as a red crystalline solid (0.35 g, 63%). $^1$H NMR (C$_6$D$_6$, 300 MHz): 7.25, 6.88 (m, 2H each, PhH), 6.83 (m, 2H, ArH), 6.80-6.67 (m, 6H, PhH), 6.56 (m, 2H, ArH), 2.84, 2.30 (d of q, 2H each, J=7.5 Hz, 7.5 Hz, CH$_2$Me), 1.70 (s, 6H, CH$_3$), 1.23 (t, 6H, J=7.5 Hz, CH$_2$CH$_3$). $^{13}$C NMR (CDCl$_3$, 125 MHz): 181.0 (C=N), 160.3 (ArC—OH), 140.0 (Ar$_F$C—F, m, $^1J_{CF}$=250 Hz), 138.9 (Ar$_F$C—F, m, $^1J_{CF}$=250 Hz), 137.7 (ArC or PhC), 137.6 (Ar$_F$C—F, m, $^1J_{CF}$=250 Hz), 136.8 (Ar$_F$C—F, m, $^1J_{CF}$=250 Hz), 136.2, 132.9, 132.5, 131.0, 130.3, 128.5, 128.4, 126.5, 126.0 (ArC or PhC), 125.6 (Ar$_F$C$_{ipso}$, m), 123.9 (ArC), 22.9 (ArCH$_2$Me), 20.9 (ArCH3), 13.9 (ArCHCH$_3$). $^{19}$F NMR (CDCl$_3$, 282 MHz): −138.1, −144.1, −158.4, −162.0, −164.6 (Ar$_F$F, m). Anal. calc. for C$_{44}$H$_{30}$N$_2$O$_2$F$_{10}$Cl$_2$Ti: C, 56.98; H, 3.26; N, 3.02. Anal. found: C, 56.76; H, 3.27; N, 2.84.

Working Example III

Synthesis of Complex 4

For ligand D (2,4-Dimethyl-6-[phenyl(pentafluorophenylimino)methyl]-phenol), N-Pentafluorophenyl-benzamide (2.82 g, 9.82 mmol) and phosphorous pentachloride (2.04 g, 9.82 mmol) were combined as described above to give the imidoyl chloride, which was reacted with aluminum chloride (1.57 g, 11.8 mmol) and 2,4-dimethylphenol (1.19 mL, 9.82 mmol) as described above to give the crude product as a yellow oil. This was recrystallized from methanol at −20° C. to give ligand D as a yellow crystalline solid (1.82 g, 47%). $^1$H NMR (CDCl$_3$, 400 MHz): 7.42-7.34 (m, 3H, PhH), 7.17 (m, 3H, PhH and ArH), 6.65 (m, 1H, ArH), 2.32, 2.13 (s, 3H each, CH$_3$). $^{13}$C NMR (CDCl$_3$, 125 MHz): 181.6 (C=N), 159.0 (ArC—OH), 138.7 (Ar$_F$C—F, m, $^1J_{CF}$=244 Hz), 138.0 (Ar$_F$C—F, m, $^1J_{CF}$=250 Hz), 137.7 (Ar$_F$C—F, m, $^1J_{CF}$=250 Hz), 137.3, 135.0, 130.7, 130.0, 128.6, 127.2, 127.1, 127.0 (ArC or PhC), 123.9 (Ar$_F$C$_{ipso}$m), 118.2 (ArC), 20.6, 16.0 (ArCH$_3$). $^{19}$F NMR (CDCl$_3$, 282 MHz): −149.6, −161.2, −163.3 (Ar$_F$F, m). Anal. calc. for C$_{21}$H$_{14}$NOF$_5$: C, 64.45; H, 3.61; N, 3.58. Anal. found: C, 64.22; H, 3.84; N, 3.48.

For complex 4 (Bis[2,4-Dimethyl-6-[phenyl(pentafluorophenylimino)methyl]-phenolato]dichlorotitanium), ligand D (0.50 g, 1.28 mmol) was reacted with n-butyllithium solution (0.84 mL, 1.34 mmol) and TiCl$_4$ solution (0.64 mL, 0.64 mmol) as described above to give 4 as a red crystalline solid (0.38 g, 58%). $^1$H NMR (C$_6$D$_6$, 300 MHz): 7.22, 6.92 (m, 2H each, PhH), 6.79-6.70 (m, 6H, PhH), 6.67, 6.53 (m, 2H each, ArH), 2.08, 1.66 (s, 6H each, CH$_3$). $^{13}$C NMR (CDCl$_3$, 125 MHz): 180.9 (C=N), 160.6 (ArC—OH), 140.0 (Ar$_F$C—F, m, $^1J_{CF}$=250 Hz), 139.5 (ArC or PhC), 138.9 (Ar$_F$C—F, m, $^1J_{CF}$=250 Hz), 137.6 (Ar$_F$C—F, m, $^1J_{CF}$=250 Hz), 136.7 (Ar$_F$C—F, m, $^1J_{CF}$=250 Hz), 136.1, 133.0, 130.8, 130.3, 128.6, 128.5, 126.4, 126.3, 126.0 (ArC or PhC), 125.5 (Ar$_F$C$_{ipso}$, m), 123.8 (ArC), 20.8, 15.5 (ArCH$_3$). $^{19}$F NMR (CDCl$_3$, 282 MHz): −138.2, −144.1, −158.4, −161.9, −164.6 (Ar$_F$F, m). Anal. calc. for C$_{42}$H$_{26}$N$_2$O$_2$F$_{10}$Cl$_2$Ti: C, 56.09; H, 2.91; N, 3.11. Anal. found: C, 56.38; H, 2.87; N, 2.94.

Working Example IV

Synthesis of Polypropylene Homopolymer

A general procedure for propylene polymerizations that was used is as follows: A six-ounce Lab-Crest pressure reaction vessel (Andrews Glass) equipped with a magnetic stir bar was charged with dry PMAO-IP (150 equivalents Al per Ti) and toluene (100 mL). The reactor was then equilibrated at 0° C. and the solution was saturated with propylene (30 psi). A toluene solution (5 mL) of PHI catalyst (0.01-0.03 mmol) was injected via syringe to initiate the polymerization. A constant pressure of propylene (30 psi) was maintained throughout the polymerization. After an appropriate time (3.0 hours) at 0° C., the reaction was quenched with methanol (5 mL) and the reactor was vented. The polymer was precipitated in copious methanol/HCl (1% acid, 300 mL), collected, washed with methanol, and dried to constant weight.

Table I below shows reaction amounts and conditions and results.

Polypropylenes produced by catalysts 2-4 are not completely regioregular: the NMR spectra contain small peaks arising from head-to-head and tail-to-tail misinsertions (<5%). There are no olefin peaks in the NMR spectra, suggesting that β-H and β-alkyl elimination reactions do not occur during the polymerization.

Of the catalysts tested, complex 4 produced polypropylene with the highest isotacticity and was used to investigate catalyst behavior further. To demonstrate the living behavior of complex 4, propylene polymerizations were carried out from 1 to 10 hours at 0° C. The molecular weight increased linearly with polymer yield, and $M_w/M_n$ values were consistently narrow for all polymerizations.

Working Example V

Synthesis of Block Copolymer of the Fourth and Sixth Embodiment

To demonstrate the ability of the living catalyst to synthesize monodisperse block copolymers via sequential

TABLE 1

| Complex | Method[b] | $T_{rxn}$ (C.) | Yield (g) | TOF $(h^{-1})$[c] | $M_n(g/mol)$[d] | $M_w/M_n$[d] | Tacticity[e] [m⁴] | [r⁴] | $\alpha$[f] | $T_g(C.)$[g] | $T_m(C.)$[g] |
|---|---|---|---|---|---|---|---|---|---|---|---|
| 1[h] | A | 0 | 0.16 | 9 | Bimodal | Broad | 0.07 | 0.26 | NA[k] | −8.6 | ND[l] |
| 2 | A | 0 | 0.13 | 35 | 2710 | 1.12 | 0.46 | <0.01 | 0.85 | −18.4 | ND[l] |
| 3 | A | 0 | 0.40 | 105 | 7290 | 1.17 | 0.45 | <0.01 | 0.85 | −14.1 | ND[l] |
| 4 | A | 0 | 1.11 | 293 | 27 940 | 1.11 | 0.53 | <0.01 | 0.89 | −12.5 | 69.5 |
| 5 | A | 0 | 1.22 | 323 | 35 440 | 1.12 | 0.08 | 0.13 | NA[k] | −5.5 | ND[l] |
| 6[i] | A | 0 | 2.05 | 1690 | 123 100 | 1.13 | <0.01 | 0.22 | NA[k] | −2.9 | ND[l] |
| 4[j] | B | −20 | 0.44 | 41 | 33 700 | 1.15 | 0.61 | <0.01 | 0.91 | −12.9 | 96.4 |
| 4 | B | 0 | 0.17 | 138 | 13 580 | 1.16 | 0.54 | <0.01 | 0.89 | −13.8 | 70.1 |
| 4 | B | 20 | 0.32 | 267 | 16 760 | 1.13 | 0.48 | <0.01 | 0.85 | −12.0 | ND[l] |
| 4 | B | 50 | 1.23 | 967 | 59 370 | 1.10 | 0.27 | 0.02 | 0.77 | −9.2 | ND[l] |

[a]General conditions: Catalyst in toluene (5 mL) was added to a propylene-saturated PMAO-IP solution (100 mL of toluene; [Al]/[Ti] = 150) for 3.0 h.
[b]Method A: 0.03 mmol of catalyst, reactor pressure maintained at 30 psi during polymerization. Method B: 0.01 mmol catalyst, closed reactor to maintain a constant initial [propylene] at different temperatures.
[c]Turnover frequency (TOF): mol propylene/(mol Ti · h).
[d]Determined using gel permeation chromatography in 1,2,4-$C_6H_3$ at 140° C. versus polyethylene standards.
[e]Determined by integration of the methyl region of the $^{13}C$ NMR spectrum.
[f]Enantiofacial selectivity parameter, calculated from the $^{13}C$ NMR spectrum using the equation $[m^4] = \alpha^5 + (1 - \alpha)^5$.
[g]Determined using differential scanning calorimetry (2$^{nd}$ heating).
[h]$t_{rxn}$ = 15.0 h.
[i]0.01 mmol 6.
[j]$t_{rxn}$ = 24.0 h.
[k]Not applicable; data does not fit site control statistics.
[l]None detected.

Complexes 1-6 contain ligands with N-pentafluorophenyl groups and were synthesized using previously reported procedures, such as those disclosed in Tian, J; Hustad, P. D.; Coates, G. W. *J. Am. Chem. Soc.* 2001, 123, 5134-35 and Reinartz, S.; Mason A. F.; Lobkovsky, E. B.; Coates, G. W. *Organometallics* 2003, 22, 2542-2544. Complexes 2, 3 and 4 were synthesized as described in Working Examples I, II and II, respectively. Ketimine complexes 1-5 have $R^3$=Ph and have ortho-phenol substituents that decrease in size from $R^1$=$^t$Bu to $R^1$=H. Phenoxyaldimine ($R^3$=H) complex 6 can be compared to complex 4. When activated with MAO, complexes 1-6 were active catalysts for propylene polymerization. Catalysts 2-4 produced polypropylenes that are substantially isotactic. All catalysts except for 1 formed polypropylene with narrow molecular weight distributions indicative of living behavior ($M_w/M_n \leq 1.17$). As with aldimine catalysts, activity increases as the size of $R^1$ decreases.

monomer addition, an isotactic polypropylene-block-ethylene/propylene diblock copolymer was synthesized using complex 4. Narrow molecular weight distributions (both $M_w/M_n$=1.10) were measured for both the initial isotactic polypropylene block ($M_n$=28.1 kg/mol) and the final diblock product ($M_n$=62.0 kg/mol).

Working Example VI

Effect of Temperature

The effect of temperature on polymerization behavior was also investigated. The following procedure was used. A slightly different procedure was used for variable temperature propylene polymerizations to ensure that the propylene concentration remained relatively constant over the temperature range investigated (−40° C. to 50° C.). A six-ounce Lab-Crest pressure reaction vessel (Andrews Glass)

equipped with a magnetic stir bar was charged with dry PMAO-IP (150 equivalents Al per Ti) and toluene (100 mL). The reactor was then equilibrated at 0° C. under 30 psi of propylene for one hour. The reactor was disconnected from the propylene feed and was warmed or cooled to the desired polymerization temperature. A toluene solution (5 mL) of PHI catalyst (0.01 mmol) was quickly injected via syringe to initiate the polymerization. The sealed reactor was stirred for 3.0 hours at the desired temperature, then the reaction was quenched with methanol (5 mL) and the reactor was vented. The polymer was precipitated in copious methanol/HCl (1% acid, 300 mL), collected, washed with methanol, and dried to constant weight. The results are summarized in Table 1 above. Activity and molecular weight both increased with increasing temperature, and molecular weight distributions remained narrow. At low temperatures, isotacticity increased but catalyst activity was greatly reduced. Molecular weight increased linearly with polymer yield, and $M_w/M_n$ values were consistently narrow for all polymerizations.

Working Example VII

Synthesis of Copolymer of the Second Embodiment, Namely Poly(propylene-co-ethylene)

A six-ounce Lab-Crest pressure reaction vessel (Andrews Glass) equipped with a magnetic stir bar is charged with dry PMAO-IP (150 equivalents Al per Ti) and toluene (100 mL). The reactor is then equilibrated at 0° C. and the solution is saturated with propylene (30 psi), then ethylene is added at 35 psi. A toluene solution (5 mL) of complex 4 (0.02 mmol) is injected via syringe to initiate the copolymerization. A constant pressure of ethylene (35 psi) is maintained throughout the polymerization. After an appropriate time (10 minutes) at 0° C., the reaction is quenched with methanol (5 mL) and the reactor is vented. The polymer is precipitated in copious methanol/HCl (1% acid, 300 mL), collected, washed with methanol, and dried to constant weight.

Working Example VIII

Synthesis of Copolymer of the Third Embodiment, Namely isotactic-polypropylene-block-atactic-polypropylene A six-ounce Lab-Crest pressure reaction vessel (Andrews Glass) equipped with a magnetic stir bar is charged with dry PMAO-IP (150 equivalents Al per Ti) and toluene (100 mL). The reactor is then equilibrated at 0° C. and the solution is saturated with propylene (30 psi). The reactor is cooled to −20° C., and a toluene solution (5 mL) of complex 4 (0.02 mmol) is injected via syringe to initiate the copolymerization. After an appropriate time (3 hours) at −20° C., the reaction is warmed to 70° C. for 1 hour, then is quenched with methanol (5 mL) and the reactor is vented. The polymer is precipitated in copious methanol/HCl (1% acid, 300 mL), collected, washed with methanol, and dried to constant weight.

Working Example IX

Synthesis of Block Copolymer of the Fifth Embodiment, Isotactic-polypropylene-block-polyethylene A six-ounce Lab-Crest pressure reaction vessel (Andrews Glass) equipped with a magnetic stir bar was charged with dry PMAO-IP (150 equivalents Al per Ti) and toluene (100 mL). The reactor was then equilibrated at 0° C. and the solution was saturated with propylene (30 psi). The reactor was cooled to −20° C., and a toluene solution (5 mL) of complex 4 (0.04 mmol) was injected via syringe to initiate the copolymerization. After an appropriate time (4 hours) at −20° C., the reaction was subjected to vacuum to remove propylene. Ethylene was then added to the reaction vessel at 35 psi, and the reaction was continued for 3 minutes. The reaction was then quenched with methanol (5 mL) and the reactor was vented. The polymer was precipitated in copious methanol/HCl (1% acid, 300 mL), collected, washed with methanol, and dried to constant weight. The resultant diblock copolymer had an overall $M_n$ of 176,000 g/mol and a PDI of 1.12, with a propylene content of 7 mole percent.

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. Polypropylene homopolymer having a number average molecular weight ranging from 1,000 to 1,000,000, an isotacticity defined by a [mmmm] pentad content greater than 0.20 and having a PDI less than 1.2.

2. Polypropylene random or tapered copolymer where comonomer is selected from the group consisting of ethylene and $C_4$-$C_{20}$ alpha olefin, having a number average molecular weight ranging from 1,000 to 1,000,000 and a PDI less than 1.5 and an isotacticity for $C_3$-$C_{20}$ alpha olefin segments defined by a [mmmm] pentad content greater than 0.20.

3. Block copolymer having one to five polypropylene blocks with an isotacticity defined by a [mmmm] pentad content greater than 0.20 and a PDI of less than 1.8 and having number average molecular weight ranging from 1,000 to 1,000,000, and one to five atactic polypropylene blocks having number average molecular weight ranging from 1,000 to 1,000,000.

4. Block copolymer having one or more polypropylene blocks with an isotacticity defined by a [mmmm] pentad content greater than 0.20 and having a PDI of less than 1.8 and having a number average molecular weight ranging from 1,000 to 1,000,000, and one or more blocks that are not solely polyethylene or polypropylene having a number average molecular weight ranging from 1,000 to 1,000,000.

5. The block copolymer of claim 4 where the non-homopolyethylene block(s) are of ethylene/propylene copolymer.

6. Block copolymer having one polypropylene block having isotacticity defined by [mmmm] pentad content greater than 0.2 and having a number average molecular weight of at least 1,000 and one polyethylene block having a number average molecular weight of at least 1,000, where the block copolymer has PDI less than 1.2 and number average molecular weight ranging from 2,000 to 6,500 g/mol or has a PDI less than 1.3 and number average molecular weight ranging from greater than 6,500 to 22,000 g/mol or has PDI of less than 2 and a number average molecular weight ranging from greater than 22,000 to 1,000,000.

* * * * *